(12) United States Patent
Liniger

(10) Patent No.: US 12,018,229 B2
(45) Date of Patent: Jun. 25, 2024

(54) ORGANIC COMPOUNDS

(71) Applicant: Givaudan SA, Vernier (CH)

(72) Inventor: Marc Liniger, Embrach (CH)

(73) Assignee: Givaudan SA, Vernier (CH)

( * ) Notice: Subject to any disclaimer, the term of this patent is extended or adjusted under 35 U.S.C. 154(b) by 608 days.

(21) Appl. No.: 17/286,216

(22) PCT Filed: Oct. 16, 2019

(86) PCT No.: PCT/EP2019/078045
§ 371 (c)(1),
(2) Date: Apr. 16, 2021

(87) PCT Pub. No.: WO2020/079052
PCT Pub. Date: Apr. 23, 2020

(65) Prior Publication Data
US 2021/0355411 A1    Nov. 18, 2021

(30) Foreign Application Priority Data

Oct. 18, 2018 (GB) ..................................... 1816948

(51) Int. Cl.
*C11B 9/00* (2006.01)
*C07D 309/18* (2006.01)

(52) U.S. Cl.
CPC ............ *C11B 9/008* (2013.01); *C07D 309/18* (2013.01)

(58) Field of Classification Search
CPC ............................... C07D 309/18; C11B 9/008
USPC .................................................... 512/11, 8, 1
See application file for complete search history.

(56) References Cited

U.S. PATENT DOCUMENTS 9,399,751 B1    7/2016 Closson et al.

FOREIGN PATENT DOCUMENTS

| EP | 1927593 A1 | 6/2008 | |
| EP | 3072501 A1 * | 9/2016 | ............... A61K 8/33 |
| EP | 3072501 A1 | 9/2016 | |
| SU | 1108093 A1 | 8/1984 | |

OTHER PUBLICATIONS

Great Britain Search Report for Application No. 1816948.2 dated Apr. 17, 2019.
International Search Report for Application No. PCT/EP2019/078045 dated Feb. 3, 2020.
Written Opinion of the International Searching Authority for Application No. PCT/EP2019/078045 dated Feb. 3, 2020.
Jianke LI, et al., Synthesis of tetrahydropyran derivatives via a novel indium trichloride mediated cross-cyclization between epoxides and homoallyl alcohols, Tetrahedron Letters, Nov. 2000, pp. 793-796, vol. 42, Elsevier Science Ltd.
Verena Weidmann et al., Variants of the Prins Cyclization for the Synthesis of Terpenoid Spiroethers and Oxabicyclo [3.3.1]Nonane Derivatives, The Journal of Organic Chemistry, 2014, pp. 10123-10131, vol. 79, American Chemical Society.
Kyohei Fujiwara, et al., Cationic Iron(III) Porphyrin-Catalyzed [4+2] Cycloaddition of Unactivated Aldehydes with Simple Dienes, Journal of the American Chemical Society, 2012, pp. 5512-5515, vol. 134, American Chemical Society.

* cited by examiner

*Primary Examiner* — Jessica Whiteley
(74) *Attorney, Agent, or Firm* — Curatolo Sidoti & Trillis Co., LPA; Salvatore A. Sidoti; Floyd Trillis, III

(57) ABSTRACT

The present invention refers to dihydropyran derivatives, and to a process of making the same. The invention further refers to perfume compositions and fragranced articles comprising them.

12 Claims, No Drawings

ORGANIC COMPOUNDS

CROSS REFERENCE TO RELATED APPLICATIONS

This application is a national stage application of International Application No. PCT/EP2019/078045, filed 16 Oct. 2019, which claims priority from Great Britain Patent Application No. 1816948.2, filed 18 Oct. 2018, both of which applications are incorporated herein by reference in their entireties.

The present invention relates to dihydropyran derivatives possessing powerful green, floral olfactory properties. The invention furthermore refers to methods for their production, and to fragrance compositions containing these.

In the fragrance and flavor industry, perfumers and flavorists are continually looking for new compounds of high impact odors, or imparting new odor notes.

Compounds possessing powerful green, floral, natural odor profiles are very attractive as widely suitable odor notes, especially for the use in fabric care products.

Dihydropyran derivatives have been described in literature. Some have been described to be suitable as fragrance ingredients. U.S. Pat. No. 4,070,491 describes the use of 2-alkyl-4-aryldihydropyrans (A) for augmenting the organoleptic properties of foodstuffs and tobacco.

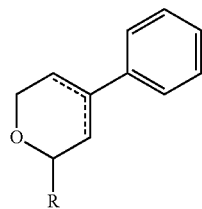

(A)

Pyran derivatives are also described by Jianke Li et al., Tetrahedron Letters, Volume 42, 793-796 (2001). They are used as intermediates for the preparation of antibiotics. However, organoleptic properties of such compounds are not set forth.

Surprisingly, we have now found a new class of dihydropyran derivatives that possess very powerful green, floral notes. In particular it was surprisingly found that dihydropyran derivatives of formula (I) as defined herein below possess a remarkable low odor threshold value compared to the corresponding dihydropyran derivatives wherein the two rings are linked by a C2 or C4 alkyl chain (i.e. compounds of formula (I) wherein n is 2 or 4).

As used herein, "odor threshold value" means the lowest concentration of a vapour in the air which can be detected by smell. Generally speaking, it can be said that a compound with a low odor threshold value is more powerful than a compound with a high odor threshold value and thus allows the use of very low concentration in a fragrance composition to achieve an olfactory effect.

There is provided in a first embodiment the use as fragrance of a compound of formula (I)

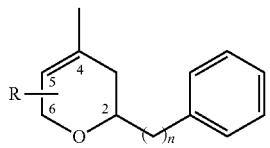

(I)

wherein R is hydrogen or methyl at C-5 or C-6, and n is 1 or 3.

The compounds of formula (I) comprise one or more chiral centers and as such may exist as a mixture of stereoisomers, or they may be resolved as isomerically pure forms. Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methods known in the art, e.g. preparative HPLC and GC, crystallization or stereoselective synthesis.

In one particular embodiment the compound is a compound of formula (I) wherein n is 3.

As a specific example of compounds of formula (I), one may cite, as non-limiting example, 4-methyl-2-(3-phenylpropyl)-3,6-dihydro-2H-pyran, which possesses a very powerful, green, earthy, stemone, bell pepper, petitgrain, sligthly rosy odor character.

Further, non-limiting examples are compounds of formula (I) wherein n is 3.

Further, non-limiting examples are compounds of formula (I) selected from 4,6-dimethyl-2-(3-phenylpropyl)-3,6-dihydro-2H-pyran; 4,5-dimethyl-2-(3-phenylpropyl)-3,6-dihydro-2H-pyran; 2-benzyl-4-methyl-3,6-dihydro-2H-pyran; 2-benzyl-4,6-dimethyl-3,6-dihydro-2H-pyran; and 2-benzyl-4,5-dimethyl-3,6-dihydro-2H-pyran.

The compounds of formula (I) may be used alone, as stereoisomeric mixture, or in combination with known odorant molecules selected from the extensive range of natural products, and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art. As used herein, "carrier material" means a material which is practically neutral from a odorant point of view, i.e. a material that does not significantly alter the organoleptic properties of odorants.

The term "auxiliary agent" refers to ingredients that might be employed in a fragrance composition for reasons not specifically related to the olfactive performance of said composition. For example, an auxiliary agent may be an ingredient that acts as an aid to processing a fragrance ingredient or ingredients, or a composition containing said ingredient(s), or it may improve handling or storage of a fragrance ingredient or composition containing same. It might also be an ingredient that provides additional benefits such as imparting color or texture. It might also be an ingredient that imparts light resistance or chemical stability to one or more ingredients contained in a fragrance composition. A detailed description of the nature and type of adjuvants commonly used in fragrance compositions containing same cannot be exhaustive, but it has to be mentioned that said ingredients are well known to a person skilled in the art.

As used herein, 'fragrance composition' means any composition comprising the compound of formula (I) and a base material, e.g. a diluent conventionally used in conjunction with odorants, such as diethyl phthalate (DEP), dipropylene glycol (DPG), isopropyl myristate (IPM), pentane-1,2-diol, triethyl citrate (TEC) and alcohol (e.g. ethanol). Optionally, the composition may comprise an anti-oxidant adjuvant. Said anti-oxidant may be selected from Tinogard® TT (BASF), Tinogard® Q (BASF), Tocopherol (including its isomers, CAS 59-02-9; 364-49-8; 18920-62-2; 121854-78-2), 2,6-bis(1,1-dimethylethyl)-4-methylphenol (BHT, CAS 128-37-0) and related phenols, hydroquinones (CAS 121-31-9).

The following list comprises examples of known odorant molecules, which may be combined with the compounds of formula (I):

essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;

alcohols, e.g. cinnamic alcohol ((E)-3-phenylprop-2-en-1-ol); cis-3-hexenol ((Z)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol); ethyl linalool ((E)-3,7-dimethylnona-1,6-dien-3-ol); farnesol ((2E,6Z)-3,7,11-trimethyldodeca-2,6,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-trimethylcyclopent-3-en-1-yl)pentan-2-ol); terpineol (2-(4-methylcyclohex-3-en-1-yl)propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;

aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl) ethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yl)ethanone); Isoraldeine® ((E)-3-methyl-4-(2,6,6-trimethylcyclohex-2-en-1-yl)but-3-en-2-one); Hedione® (methyl 3-oxo-2-pentylcyclopentaneacetate); 3-(4-isobutyl-2-methylphenyl)propanal; maltol; methyl cedryl ketone; methylionone; verbenone; and/or vanillin;

ether and acetals, e.g. Ambrox® (3a,6,6,9a-tetramethyl-2,4,5,5a,7,8,9,9b-octahydro-1 H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2%2%3,7,7-pentamethylspiro[bicyclo[4.1.0]heptane-2,5'-[1,3]dioxane]);

esters and lactones, e.g. benzyl acetate; cedryl acetate ((1S,6R,8aR)-1,4,4,6-tetramethyloctahydro-1H-5,8a-methanoazulen-6-yl acetate); γ-decalactone (6-pentyltetrahydro-2H-pyran-2-one); Helvetolide® (2-(1-(3,3-dimethylcyclohexyl)ethoxy)-2-methylpropyl propionate); γ-undecalactone (5-heptyloxolan-2-one); and/or vetiveryl acetate ((4,8-dimethyl-2-propan-2-ylidene-3,3a,4,5,6,8a-hexahydro-1H-azulen-6-yl) acetate);

macrocycles, e.g. Ambrettolide ((Z)-oxacycloheptadec-10-en-2-one); ethylene brassylate (1,4-dioxacycloheptadecane-5,17-dione); and/or Exaltolide® (16-oxacyclohexadecan-1-one); and heterocycles, e.g. isobutylquinoline (2-isobutylquinoline).

In one particular embodiment compounds of formula (I) may be combined with compounds of formula (II)

$$(II)$$

wherein
R is hydrogen or methyl,
n is 1 or 3, and
one of the dashed lines is a carbon-carbon double bond and the other dashed line is a carbon-carbon single bond.

In certain embodiments the compounds of formula (I) may be combined with compounds of formula (II) in a ratio of from 1:99 to 99:1. In certain embodiments the compounds of formula (I) may be combined with compounds of formula (II) in a ratio of 1: 9 to 9:1. In certain embodiments the compounds of formula (I) may be combined with compounds of formula (II) in a ratio of 1:5 to 5:1 (e.g. the ratio of a compound of formula (I) : compound of formula (II) is 1:4 or 1:3).

In another particular embodiment the compound of formula (I) and the compound of formula (II) when combined are compounds wherein R is hydrogen and n is 3.

In certain embodiments the compound of formula (I) wherein R is hydrogen and n is 3 may be combined with a compound of formula (II) wherein R is hydrogen and n is 3 in a ratio from 1:99 to 99:1 (e.g. 1:9 to 9:1, 1:5 to 5:1, such as 1:4 or 1:3). In certain embodiments the compound of formula (II) is a mixture of 4-methylen-2-(3-phenylpropyl) tetrahydro-2H-pyran and 4-methyl-6-(3-phenylpropyl)-3,6-dihydro-2H-pyran.

The compound according to formula (I) either alone or, e.g. as mixture with compounds of formula (II), may be used in a broad range of fragranced articles, e.g. in any field of fine and functional perfumery, such as perfumes, air care products, household products, laundry products, body care products and cosmetics. The compound can be employed in widely varying amounts, depending upon the specific article and on the nature and quantity of other odorant ingredients. The proportion is typically from 0.0001 to 3 weight per cent of the article. In one embodiment, the compound of the present invention may be employed in a fabric softener in an amount from 0.001 to 0.3 weight per cent (e.g. 0.01 to 0.1 including 0.05 weight %). In another embodiment, the compound of formula (I) or as admixture with compounds of formula (II), may be used in fine perfumery in amounts from 0.01 to 30 weight per cent (e.g. up to about 10 or up to 20 weight per cent), more preferably between 0.01 and 5 weight per cent. However, these values are given only by way of example, since the experienced perfumer may also achieve effects or may create novel accords with lower or higher concentrations.

In one embodiment there is provided a fragranced article comprising an acceptable amount of at least one compound of formula (I), a mixture thereof, or admixed with compound(s) of formula (II). For example, the fragrance article may comprise 0.000001 weight % to 90 weight % (including 0.00001 weight %; 0.0001 weight %, 0.001 weight %, 0.01 weight %, 0.05 weight %, 0.1 weight %, 0.5 weight %, 1 weight %, 5 weight %, 8 weight %, 10 weight %, 15 weight %, 20 weight %, 25 weight %, 30 weight %, 50 weight %, 60 weight %, 65 weight %) based on the total amount of the article.

The compounds as described hereinabove may be employed in a consumer product base simply by directly mixing the compound of formula (I), or a fragrance composition comprising the compound of formula (I), or a mixture thereof, with the consumer product base, or it may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, and then mixed with the consumer product base.

Thus, the invention additionally provides a method of manufacturing a fragranced article, comprising the incorporation of a compound of formula (I), as a fragrance ingredient, either by directly admixing the compound to the consumer product base or by admixing a fragrance composition comprising the compound of formula (I), which may then be mixed with a consumer product base, using conventional techniques and methods. Through the addition of an olfactory acceptable amount of the compound of the present invention as hereinabove described the odor notes of a consumer product base will be improved, enhanced, or modified.

Thus, the invention furthermore provides a method for improving, enhancing or modifying a consumer product base by means of the addition thereto of an olfactorily acceptable amount of the compound of formula (I).

The invention also provides a fragranced article comprising:
a) as odorant the compound of formula (I), or a mixture thereof; and
b) a consumer product base.

As used herein, 'consumer product base' means a composition for use as a consumer product to fulfill specific actions, such as cleaning, softening, and caring or the like.

Examples of such products include fine perfumery, e.g. perfume and eau de toilette; fabric care, household products and personal care products such as cosmetics, laundry care detergents, rinse conditioner, personal cleansing composition, detergent for dishwasher, surface cleaner; laundry products, e.g. softener, bleach, detergent; body-care products, e.g. shampoo, shower gel; air care products (includes products that contain preferably volatile and usually pleasant-smelling compounds which advantageously can even in very small amounts mask unpleasant odors). Air fresheners for living areas contain, in particular, natural and synthetic essential oils such as pine needle oils, citrus oil, eucalyptus oil, lavender oil, and the like, in amounts for example of up to 50% by weight. As aerosols they tend to contain smaller amounts of such essential oils, by way of example less than 5% or less than 2% by weight, but additionally include compounds such as acetaldehyde (in particular, <0.5% by weight), isopropyl alcohol (in particular, <5% by weight), mineral oil (in particular, <5% by weight), and propellants.

Cosmetic products include:
(a) cosmetic skincare products, especially bath products, skin washing and cleansing products, skincare products, eye makeup, lip care products, nail care products, intimate care products, foot care products;
(b) cosmetic products with specific effects, especially sunscreens, tanning products, de-pigmenting products, deodorants, antiperspirants, hair removers, and shaving products;
(c) cosmetic dental-care products, especially dental and oral care products, tooth care products, cleaners for dental prostheses, adhesives for dental prostheses; and
(d) cosmetic hair care products, especially hair shampoos, hair care products, hair setting products, hair-shaping products, and hair coloring products.

This list of products is given by way of illustration, and is not to be regarded as being in any way limiting.

Whereas some compounds falling under the general formula (I) as hereinabove defined have been described in literature, some have not been described in literature, and are thus novel in their own right.

Thus, in another aspect of the invention, there is provided a compound of formula (I) in the form of any one of its stereoisomers or a mixture thereof

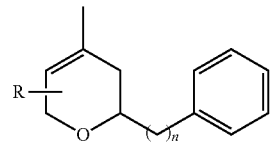

(I)

wherein
n is 3, and
R is hydrogen or methyl.

The compounds of formula (I) may, for example, be prepared by a hetero Diels-Alder reaction of an aryl aldehyde and a 1,3-diene (e.g. isoprene) or a Prins reaction of an aryl aldehyde and a homoallylic alcohol (e.g. isoprenol), under conditions known to the person skilled in the art.

The invention is now further described with reference to the following non-limiting examples. These examples are for the purpose of illustration only and it is understood that variations and modifications can be made by one skilled in the art.

All products were purified after work-up by either flash chromatography (FC) using Tsingdao Haiyang Chemical silica gel (200±300 mesh) and silica gel Merck grade (60 Å) or distillation. Unless otherwise noted, a mixture of isohexane:MTBE (10:1) was used as eluent. NMR spectra were measured in $CDCl_3$ and are reported relative to TMS ($^1$H NMR spectrum) or relative to $CDCl_3$ ($^{13}$C NMR spectrum) as follows: chemical shifts (δ ppm), coupling constants J in Hz. GC-MS analysises were run on a MSD5975mass spectrometer and are reported as m/z list (relative intensity). Odor description refers to the odor of the isomeric mixture of the compounds unless otherwise indicated.

EXAMPLE 1

4-Methyl-2-(3-phenylpropyl)-3,6-dihydro-2H-pyran

To a solution of 4-phenylbutanal (3.0 g, 20.2 mmol, 1.0 equiv) and isoprene (1.52 g, 22.3 mmol, 1.1 equiv) in CH$_2$Cl$_2$ (50 mL) was added dropwise at room temperature a solution of Et$_2$AlCl (30.4 mL, 30.4 mmol, 1.5 equiv, 1.0 M in hexanes). After stirring for 5 h at room temperature, the reaction mixture was poured onto ice and extracted with hexanes. The organic layer was washed with water, sat. NaHCO$_3$ and brine. The combined organic extracts were dried over MgSO$_4$, filtered and concentrated under reduced pressure to give a crude product (4.1 g). After Kugelrohr distillation (140° C./0.08 mbar) of the crude, the collected fraction was further purified by column chromatography (hexanes/MTBE 19:1) and a second Kugelrohr distillation (140° C./0.08 mbar) to afford 4-methyl-2-(3-phenylpropyl)-3,6-dihydro-2H-pyran (2.1 g, 48% yield) as a colorless oil.

$^1$H NMR (400 MHz, CDCl$_3$): δ 7.32-7.17 (m, 5H), 5.44-5.40 (m, 1H), 4.21-4.09 (m, 2H), 3.52-3.45 (m, 1H), 2.67 (t, J=7.5 Hz, 2H), 2.01-1.80 (m, 3H), 1.78-1.60 (m, 2H), 1.71 (s, 3H), 1.58-1.49 (m, 1H) ppm. $^{13}$C NMR (101 MHz, CDCl$_3$): δ 142.4, 131.7, 128.4, 128.2, 125.6, 119.7, 73.6, 65.8, 35.9 (2CH$_2$), 35.5, 27.4, 22.9 ppm. GC-MS (EI) m/z (%): 216 (0, [M]$^{+}$), 147 (19), 105 (16), 104 (100), 99 (18), 97 (19), 91 (86), 69 (26), 68 (18), 67 (20), 41 (24).

Odor description: green, earthy, stemone, bell pepper, petitgrain, sligthly rosy.

EXAMPLE 2

4,6-Dimethyl-2-(3-phenylpropyl)-3,6-dihydro-2H-pyran

To a solution of 4-phenylbutanal (3.3 g, 22.3 mmol, 1.0 equiv) and 2-methylpenta-1,3-diene (2.68 g, 24.5 mmol, 1.1 equiv) in CH$_2$Cl$_2$ (50 mL) was added dropwise at room temperature a solution of Et$_2$AlCl (33.4 mL, 33.4 mmol, 1.5 equiv, 1.0 M in hexanes). After stirring for 5 h at room temperature, the reaction mixture was poured onto ice and extracted with hexanes. The organic layer was washed with water, sat. NaHCO$_3$ and brine. The combined organic extracts were dried over MgSO$_4$, filtered and concentrated under reduced pressure. The crude product (4.0 g) was purified by column chromatography (hexanes/MTBE 19:1) and Kugelrohr distillation (140° C./0.08 mbar) to give 4,6-dimethyl-2-(3-phenylpropyl)-3,6-dihydro-2H-pyran (1.2 g, 23% yield, dr 85:15) as a colorless oil.

$^1$H NMR (400 MHz, CDCl$_3$, mixture of two diastereoisomers, dr 85:15): 7.32-7.11 (m, 5H), 5.37-5.32 (m, 0.15H), 5.31-5.26 (m, 0.85H), 4.35-4.26 (m, 0.15H), 4.18-4.06 (m, 0.85H), 3.72-3.63 (m, 0.15H), 3.54-3.44 (m, 0.85H), 2.63 (s, 2H), 1.95-1.32 (m, 6H), 1.66 (brs, 3H), 1.19 (2 x d, J=6.6 Hz and 6.9 Hz, 3H). $^{13}$C NMR (101 MHz, CDCl$_3$, mixture of two diastereoisomers, dr 85:15): δ 142.5, 131.8, 131.0 (minor), 128.4, 128.3 (minor), 125.6, 125.2, 124.5 (minor), 74.0, 71.0, 68.5 (minor), 67.3 (minor), 35.9, 35.9, 35.7, 35.5 (minor), 34.9 (minor), 27.6, 27.5 (minor), 23.1 (minor), 22.8, 21.6, 20.1 (minor) ppm. GC-MS (EI) m/z (%) formajor diastereoisomer: 230 (2, [M]$^{+}$), 147 (25), 131 (28), 105 (15), 104 (68), 91 (100), 82 (17), 81 (17), 67 (24), 43 (39), 41 (16); GC-MS (EI) m/z (%) for minor diastereoisomer: 230 (2, [M]$^{+}$), 147 (28), 131 (34), 117 (15), 104 (62), 95 (16), 91 (100), 82 (17), 81 (17), 67 (22), 43 (31).

Odor description: green, pyrazine like, rooty, petitgrain, chili pepper.

EXAMPLE 3.

2-Benzyl-4-methyl-3,6-dihydro-2H-pyran

To a solution of 2-phenylacetaldehyde (10.0 g, 83.2 mmol, 1.0 equiv) and 3-methylbut-3-en-1-ol (9.24 mL, 91.6 mmol, 1.1 equiv) in toluene (100 mL) was added dropwise at room temperature a solution of BF$_3$ etherate (10.6 mL, 83.2 mmol, 1.0 equiv) in toluene (50 mL). After stirring for 30 min at room temperature, the reaction mixture was quenched with sat. NaHCO$_3$ and extracted with MTBE. The combined organic extracts were washed with water and brine, dried over MgSO$_4$, filtered and concentrated under reduced pressure. The crude product (18 g) was distilled under reduced pressure (0.04 mbar) over a Vigreux column (10 cm) to give an enriched fraction of product (4.5 g, bp 73° C. at 0.04 mbar). Further purification by column chromatography (pentane/MTBE 19:1) and Kugelrohr distillation (140° C./0.08 mbar) afforded 2-benzyl-4-methyl-3,6-dihydro-2H-pyran (2.7 g, 14% yield, 81% purity, along with 17% of 6-benzyl-4-methyl-3,6-dihydro-2H-pyran) as a colorless oil.

$^1$H NMR (400 MHz, CDCl$_3$): 7.32-7.18 (m, 5H), 5.41-5.37 (m, 1H), 4.22-4.06 (m, 2H), 3.72 (dtd, J=3.4, 6.7, 10.1 Hz, 1H), 2.96 (dd, J=6.8, 13.7 Hz, 1H), 2.73 (dd, J=6.4, 13.7 Hz, 1H), 2.06-1.94 (m, 1H), 1.81-1.72 (m, 1H), 1.65 (s, 3H). $^{13}$C NMR (101 MHz, CDCl$_3$): δ 138.5, 131.6, 129.3, 128.2, 126.1, 119.6, 74.6, 65.9, 42.4, 35.4, 22.9 ppm. GC-MS (EI) m/z (%): 188 (2, [M]$^{+}$), 97 (89), 96 (15), 92 (14), 91 (100), 69 (69), 67 (14), 65 (19), 41 (36), 39 (19), 29 (12).

Odor description: green, rosy, metallic, rose oxyde, gun powder, sharp, intense, fatty, floral.

EXAMPLE 4

(Comparison Example): 4-Methyl-2-(4-phenylbutyl)-3,6-dihydro-2H-pyran

To a solution of 5-phenylpentanal (3.0 g, 18.5 mmol, 1.0 equiv) and isoprene (1.39 g, 20.3 mmol, 1.1 equiv) in CH$_2$Cl$_2$ (20 mL) was added dropwise at room temperature a solution of Et$_2$AlCl (15.1 mL, 27.7 mmol, 1.5 equiv, 25% in toluene). After stirring for 5 h at room temperature, the reaction mixture was poured onto ice and extracted with hexanes. The organic layer was washed with water, sat. NaHCO$_3$ and brine. The combined organic extracts were dried over MgSO4, filtered and concentrated under reduced pressure. The crude product (3.1 g) was purified by column chromatography (hexanes/MTBE 19:1) and Kugelrohr distillation (160° C./0.08 mbar) to give 4-methyl-2-(4-phenylbutyl)-3,6-dihydro-2H-pyran (0.66 g, 15% yield) as a colorless oil.

$^1$H NMR (400 MHz, CDCl$_3$): 7.30-7.22 (m, 2H), 7.21-7.13 (m, 3H), 5.43-5.36 (m, 1H), 4.20-4.03 (m, 2H), 3.49-3.38 (m, 1H), 2.62 (t, J=7.7Hz, 2H), 1.99-1.87 (m, 1H), 1.85-1.75 (m, 1H), 1.72-1.35 (m, 6H), 1.67 (s, 3H). $^{13}$C NMR (101 MHz, CDCl$_3$): δ 142.6, 131.7, 128.3, 128.2, 125.6, 119.7, 73.6, 65.9, 35.9 (2CH$_2$), 35.8, 31.5, 25.2, 23.0 ppm. GC-MS (EI) m/z (%): 230 (6, [M]$^{+}$), 144 (17), 117 (30), 104 (34), 97 (22), 92 (20), 91 (100), 69 (26), 68 (17), 67 (21), 41 (24).

Odor description: weak, green, crunchy, bell pepper, floral.

EXAMPLE 5

(Comparison Example): 4-Methyl-2-phenethyl-3,6-dihydro-2H-pyran

To a solution of 3-phenylpropanal (7.39 g, 55.1 mmol, 1.0 equiv) and isoprene (4.5 g, 66.1 mmol, 1.2 equiv) in toluene (15 mL) was added dropwise at 0 ° C. a pre-mixed suspension of BF$_3$ etherate (0.99 mL, 7.87 mmol, 14 mol %) and Hünig's base EtN(iPr)$_2$ (0.30 mL, 1.76 mmol, 3 mol %). After stirring for 16 h at room temperature, the reaction mixture was poured onto ice and extracted with hexanes. The organic layer was washed with water, sat. NaHCO$_3$ and brine. The combined organic extracts were dried over MgSO4, filtered and concentrated under reduced pressure. The crude product (11 g) was purified by Kugelrohr distillation (180° C./0.08 mbar), by column chromatography (hexanes/MTBE 19:1) and a second Kugelrohr distillation (150° C./0.08 mbar) to afford 4-methyl-2-phenethyl-3,6-dihydro-2H-pyran (1.0 g, 9% yield) as a colorless oil.

$^1$H NMR (400 MHz, CDCl$_3$): 7.31-7.13 (m, 5H), 5.43-5.37 (m, 1H), 4.24-4.05 (m, 2H), 3.49-3.39 (m, 1H), 2.81 (ddd, J=13.9, 9.6, 5.4 Hz, 1H), 2.70 (ddd, J=13.8, 9.4, 7.1 Hz, 1H), 2.04-1.71 (m, 4H), 1.67 (s, 3H). $^{13}$C NMR (101 MHz, CDCl$_3$): δ 142.1, 131.7, 128.4, 128.3, 125.7, 119.7, 72.7, 65.8, 37.5, 35.9, 31.7, 22.9 ppm. GC-MS (EI) m/z (%): 202 (5, [M]$^+$), 117 (26), 105 (26), 104 (18), 92 (35), 91 (100), 69 (29), 68 (19), 67 (24), 41 (29), 39 (20).

Odor description: green, rosy, metallic, geranium leaf.

EXAMPLE 6

Mixture of 4-methylene-2-(3-phenylpropyl)tetrahydro-2H-pyran, 4-methyl-2-(3-phenylpropyl)-3,6-dihydro-2H-pyran and 4-methyl-6-(3-phenylpropyl)-3,6-dihydro-2H-pyran A pre-mixed solution of 4-phenylbutanal (9.00 g, 60.7 mmol, 1.0 equiv) and 3-methylbut-3-en-1-ol (6.13 mL, 60.7 mmol, 1.0 equiv) in toluene (40 mL) was added dropwise at reflux with a syringe pump (rate 10 mL/h) to a boiling solution of NaHSO$_4$ (15 mg, 0.2 mol %) in toluene (60 mL) attached to a Dean-Stark trap. After refluxing for 2 h, the reaction mixture was concentrated under reduced pressure. The crude was purified by fractional distillation under high vacuum (0.06 mbar) to afford a mixture of alkene isomers (6.4 g, 49% yield, bp 89 ° C. at 0.06 mbar) as a colorless oil. The mixture was composed of 78% of 4-methylene-2-(3-phenylpropyl)tetrahydro-2H-pyran, 13% of 4-methyl-2-(3-phenylpropyl)-3,6-dihydro-2H-pyran and 9% of 4-methyl-6-(3-phenylpropyl)-3,6-dihydro-2H-pyran).

Odor description: green, fatty, rooty, fig, bigaryl, stemone, bud.

Analytical data for 4-methylene-2-(3-phenylpropyl)tetrahydro-2H-pyran: $^1$H NMR (400 MHz, CDCl$_3$): 7.28-7.22 (m, 2H), 7.20-7.12 (m, 3H), 4.73-4.65 (m, 2H), 4.04 (ddd, J=11.2, 10.1, 3.9 Hz, 1H), 3.34 (ddd, J=12.2, 10.9, 2.7 Hz, 1H), 3.27-3.18 (m, 1H), 2.61 (t, J=7.4 Hz, 2H), 2.37-1.89 (m, 4H), 1.86-1.38 (m, 4H) ppm. $^{13}$C NMR (101 MHz, CDCl$_3$): δ 144.7, 142.3, 128.3, 128.2, 125.6, 108.2, 78.6, 68.6, 41.1, 35.9, 35.8, 35.2, 27.3 ppm. GC-MS (EI) m/z (%): 216 (1, [M]$^+$), 131 (14), 130 (10), 112 (17), 105 (13), 104 (100), 97 (29), 91 (37), 67 (22), 53 (9), 41 (10).

Analytical data for 4-methyl-2-(3-phenylpropyl)-3,6-dihydro-2H-pyran: see Example 1.

Analytical data for 4-methyl-6-(3-phenylpropyl)-3,6-dihydro-2H-pyran: Characteristic $^1$H NMR (400 MHz, CDCl$_3$) signals are: 5.31-5.26 (m, 1H), 3.96 (ddd, J=11.2, 5.8 2.4 Hz, 1H), 3.59 (ddd, J=11.2, 10.1, 3.9 Hz, 1H) ppm. Characteristic $^{13}$C NMR (101 MHz, CDCl$_3$) signals are: δ 73.8 (CHO), 63.4 (CH$_2$O) ppm. GC-MS (EI) m/z (%): 216 (1, [M]$^+$), 112 (40), 98 (7), 97 (100), 91 (31), 79 (9), 77 (8), 65 (8), 43 (7), 41 (17), 39 (8).

EXAMPLE 7

Determination of GC-Odor Threshold Values

According to standard procedures known to the person skilled in the art, threshold values for volatile perfumery compounds are determined on a gas chromatograph equipped with a sniff port by a panel of trained evaluators. The lowest concentration smelled by each panelist is recorded as the individual threshold value expressed in ng (absolute amount of compound delivered at the sniff port).

Under identical conditions the odor threshold value for the individual compounds was measured. The results are given below.

| Compound | formula (I) n is | odor threshold value [ng] |
|---|---|---|
| 4-Methyl-2-(3-phenylpropyl)-3,6-dihydro-2H-pyran | 3 | 0.02 |
| 4,6-Dimethyl-2-(3-phenylpropyl)-3,6-dihydro-2H-pyran | 3 | 0.03 |
| 2-Benzyl-4-methyl-3,6-dihydro-2H-pyran | 1 | 0.03 |
| 4-Methyl-2-(4-phenylbutyl)-3,6-dihydro-2H-pyran | 4 | 63 |
| 4-Methyl-2-phenethyl-3,6-dihydro-2H-pyran | 2 | 45 |

As can be seen from the results above the compounds of the present invention have an odor threshold value which is at least about 1500 times lower compared to dihydropyran derivatives wherein the two rings are linked by a C2 or C4 alkyl chain. Based on this, a significant advance is achieved because much smaller amount of the claimed compounds is required to impart the same odor intensity.

EXAMPLE 8

Fragrance Composition

| Compound/Ingredient | parts by weight 1/1000 |
|---|---|
| Benzyl acetate | 125 |
| 2-Methyl-1-phenylpropan-2-yl acetate | 12 |
| (Z)-hex-3-en-1-yl acetate | 1 |
| JASMACYCLENE (3a,4,5,6,7,7a-hexahydro-1H-4,7-methanoinden-6-yl acetate) | 125 |
| AGRUMEX (2-(tert-butyl)cyclohexyl acetate) | 10 |
| 2-Phenylethan-1-ol | 200 |
| Nonanal | 2 |
| Guaiac wood essential oil | 4 |
| Citronellol | 35 |
| alpha-Damascone | 2 |
| delta-Damascone | 2 |
| Diphenyl oxide (oxydibenzene) | 100 |
| GALAXOLIDE (4,6,6,7,8,8-hexamethyl-1,3,4,6,7,8-hexahydrocyclopenta[g]isochromene) | 60 |
| Eugenol | 4 |
| Beta Ionone | 10 |
| Diethyl Malonate | 2 |
| MYRALDENE (4-(4-methylpent-3-en-1-yl)cyclohex-3-ene-1-carbaldehyde) | 2 |
| ROSE OXIDE (4-methyl-2-(2-methylprop-1-en-1-yl)tetrahydro-2H-pyran) | 1 |
| Phenethyl 2-phenylacetate | 5 |
| ROSACETOL (2,2,2-trichloro-1-phenylethyl acetate) | 10 |
| Geraniol | 20 |
| PEONILE (2-cyclohexylidene-2-phenylacetonitrile) | 10 |
| TERPINEOL PUR | 10 |
| TETRAHYDRO LINALOL (3,7-dimethyloctan-3-ol) | 25 |

TRICYCLAL (2,4-dimethylcyclohex-3-ene-1-carbaldehyde) ... 3
Dipropyleneglycol (DPG) ... 215
4-Methyl-2-(3-phenylpropyl)-3,6-dihydro-2H-pyran (Example 1) ... 5

Total: 1000

The fragrance composition is, for example, suitable to fragrance a detergent (e.g. powder detergent) at a dosage of about 0.3wt %.

By the addition of a compound of formula (I) such as 4-methyl-2-(3-phenylpropyl)-3,6-dihydro-2H-pyran, the performance of the fragrance is clearly improved on neat and wet. The rosy character becomes more vibrant, green rosy, geranium leaf with a vibrant green which reinforces the "fresh and clean" olfactive association

The invention claimed is:

1. A method comprising utilizing a compound of formula (I) in the form of any one of its stereoisomers or a mixture thereof

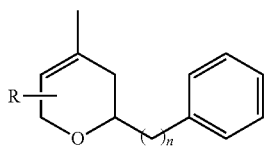

(I)

wherein R is hydrogen or methyl, and
n is 1 or 3;
as a fragrance, the method comprising mixing the compound of formula (I) with a consumer product base, or mixing a fragrance composition comprising the compound of formula (I) with a consumer product base.

2. The method of claim 1, wherein the compound of formula (I) is selected from the group consisting of 4-methyl-2-(3-phenylpropyl)-3,6-dihydro-2H-pyran, 4,6-dimethyl-2-(3-phenylpropyl)-3,6-dihydro-2H-pyran, 4,5-dimethyl-2-(3-phenylpropyl)-3,6-dihydro-2H-pyran, 2-benzyl-4-methyl-3,6-dihydro-2H-pyran, 2-benzyl-4,6-dimethyl-3,6-dihydro-2H-pyran, 2-benzyl-4,5-dimethyl-3,6-dihydro-2H-pyran, and mixtures thereof.

3. A fragrance composition comprising as odorant a compound of formula (I) as defined in claim 1 or a mixture thereof, and a base material.

4. The fragrance composition according to claim 3 further comprising a compound of formula (II)

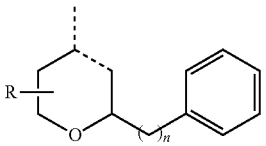

(II)

wherein R is hydrogen or methyl,
n is 1 or 3, and
one of the dashed lines is a carbon-carbon double bond and the other dashed line is a carbon-carbon single bond.

5. A fragranced article comprising as odorant a compound of formula (I) as defined in claim 1 and a consumer product base.

6. The fragranced article according to claim 5 wherein the consumer product base is selected from fine fragrance, household products, laundry products, body care products, cosmetic and air care products.

7. A compound of formula (I) in the form of any one of its stereoisomers or a mixture thereof

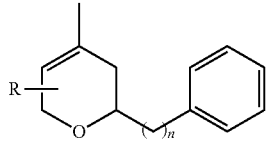

(I)

wherein
n is 3, and
R is hydrogen or methyl.

8. A method of improving, enhancing or modifying a consumer product base comprising adding thereto an olfactory acceptable amount of a compound of formula (1), or a mixture thereof

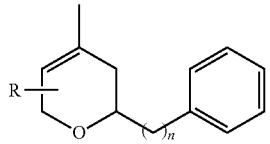

(I)

wherein R is hydrogen or methyl, and
n is 1 or 3.

9. The method according to claim 8, wherein the consumer product base is selected from the group consisting of fine fragrance, household products, laundry products, body care products, cosmetic and air care products.

10. A fragrance composition comprising as odorant a compound of formula (1) as defined in claim 2 and a base material.

11. A fragranced article comprising as odorant a fragrance composition as defined in claim 3 and a consumer product base.

12. The fragranced article according to claim 11 wherein the consumer product base is selected from fine fragrance, household products, laundry products, body care products, cosmetic and air care products.

* * * * *